US009823239B2

(12) United States Patent
Lepape et al.

(10) Patent No.: US 9,823,239 B2
(45) Date of Patent: Nov. 21, 2017

(54) PROCESS FOR DETERMINING THE SUSCEPTIBILITY TO NOSOCOMIAL INFECTIONS

(71) Applicants: HOSPICES CIVILS DE LYON, Lyons (FR); BIOMERIEUX, Marcy L'Etoile (FR)

(72) Inventors: Alain Lepape, Saint-Genis-Laval (FR); Fabienne Venet, Beynost (FR); Astrid Villars, Lyons (FR); Guillaume Monneret, Lyons (FR)

(73) Assignees: HOSPICES CIVILS DE LYON, Lyons (FR); BIOMERIEUX, Marcy L'Etoile (FR)

( * ) Notice: Subject to any disclaimer, the term of this patent is extended or adjusted under 35 U.S.C. 154(b) by 125 days.

(21) Appl. No.: 14/387,076

(22) PCT Filed: Mar. 22, 2013

(86) PCT No.: PCT/FR2013/050624
§ 371 (c)(1),
(2) Date: Sep. 22, 2014

(87) PCT Pub. No.: WO2013/140103
PCT Pub. Date: Sep. 26, 2013

(65) Prior Publication Data
US 2015/0064728 A1 Mar. 5, 2015

(30) Foreign Application Priority Data
Mar. 23, 2012 (FR) .................................. 12 52641

(51) Int. Cl.
*G01N 31/00* (2006.01)
*G01N 33/53* (2006.01)
*G01N 33/543* (2006.01)
*G01N 33/68* (2006.01)
*G01N 33/96* (2006.01)

(52) U.S. Cl.
CPC ....... *G01N 33/54306* (2013.01); *G01N 33/53* (2013.01); *G01N 33/6893* (2013.01); *G01N 33/96* (2013.01); *G01N 2333/7155* (2013.01); *G01N 2800/26* (2013.01); *G01N 2800/50* (2013.01)

(58) Field of Classification Search
None
See application file for complete search history.

(56) References Cited

FOREIGN PATENT DOCUMENTS

| FR | 2941240 A1 | 7/2010 |
| WO | 2010082004 A1 | 7/2010 |

OTHER PUBLICATIONS

Venet et al. (Critical Care, 2011, vol. 15, 231, pp. 1-9).*
Venet et al. (Electronic Poster, Berlin 2011).*
Bone et al.: "Definitions for Sepsis and Organ Failure and Guidelines for the Use of Innovative Therapies in Sepsis", accp/sccm consensus conference, Chest 1992, vol. 101, p. 1644-1655.
Crawley et al.: "Soluble IL-7Rα (sCD127) Inhibits IL-7 Activity and Is Increased in HIV Infection", The Journal of Immunology (2010); vol. 184, p. 4679-4687.
Goodwin et al.: "Cloning of the Human and Murine Interleukin-7 Receptors: Demonstration of a Soluble Form and Homology to a New Receptor Superfamily", Cell, vol. 60, p. 941-951, Mar. 23, 1990.
Janot-Sardet et al., : "A validated assay to measure soluble IL-7 receptor shows minimal impact of IL-7 treatment", Journal of Immunological Methods, vol. 353 (2010), p. 115-123.
International Search Report dated Jun. 6, 2013, corresponding to International Patent Application PCT/FR2013/050624.
Cheron A et al,: "Diminution de l'expression monocytaire de HLA-DR et risque d'infection hospitaliere", Annales Francaises D'Anesthesie et de Reanimation, Masson, Paris, FR, vol. 29, No. 5, May 1, 2010, pp. 368-376.
Caroline Landelle et al: "Low monocyte human leukocyte antigen-DR is independently associated with nosocomial infections after septic shock", Intensive Care Medicine, Springer, Berlin, DE, vol. 36, No. 11, Jul. 23, 2010, pp. 1859-1866.
Fabienne Venet et al. "Clinical review: flow cytometry perspectives in the ICU—from diagnosis of infection to monitoring of injury-induced immune dysfunctions", Critical Care, vol. 15, No. 5, Jan. 1, 2011, p. 231.
Fabienne Venet et al.: "Increased circulating regulatory T cells (CD4+CD25+CD127a) contribute to lymphocyte anergy in septic shock ptients", Intensive Care Medicine, Springer, Berlin, DE, vol. 35, No. 4, Oct. 23, 2008, pp. 678-686.
"Abstracts", Inflammation Research; Official Journal of: The International Association of Inflammation Societies the European Histamine Research Society, Birkhauser-Verlag, BA, vol. 59, No. 1, Feb. 25, 2010, pp. 9-166.

* cited by examiner

*Primary Examiner* — Lisa Cook
(74) *Attorney, Agent, or Firm* — Ladas & Parry LLP

(57) ABSTRACT

The invention relates to a process for determining the susceptibility to nosocomical infections in a patient, comprising the measurement of the expression of sCD127 in a biological sample.

11 Claims, 5 Drawing Sheets

PROCESS FOR DETERMINING THE SUSCEPTIBILITY TO NOSOCOMIAL INFECTIONS

Figure 1A:
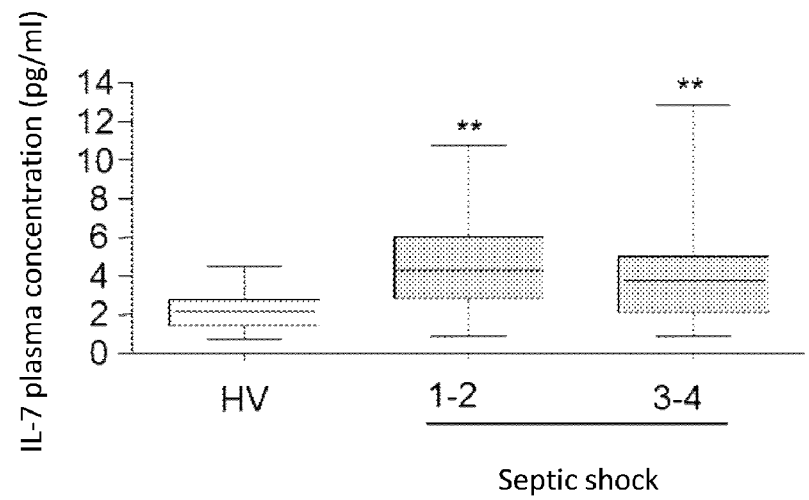

This application is a 371 of PCT/FR2013/050624, filed on Mar. 22, 2013, which claims priority to French Application No. 1252641, filed Mar. 23, 2012.

The present invention concerns the medical field in general and in particular the field of intensive care.

More specifically, the invention concerns a process for determining the susceptibility to nosocomial infections of a patient in hospital intensive care and/or having sustained an insult such as surgery, burns, trauma . . . , generating a systemic inflammatory response or SIRS, in particular a patient with sepsis, severe sepsis in particular, and preferably a patient in septic shock.

Nosocomial infections are a major public health problem. Hospitalized patients, by definition, often have reduced or deteriorated immune defences subsequent to pathologies directly damaging their immunologic competence, or due to their general condition. These patients, in particular those suffering from malnutrition or at the upper or lower age range (the elderly, infants) are especially sensitive to infections in general and in particular to the onset of nosocomial infections.

The incidence of nosocomial infections is markedly higher in intensive care units than in other hospital units. The high incidence of nosocomial infections in this sector can be accounted for by the harmful combination of several endogenous risk factors: patient exposure to invasive procedures (artificial ventilation, urinary and other catheterization), the seriousness of patient condition (and associated co-morbidities) and treatments (multiple transfusions, sedation). Nevertheless, despite all the hygiene and monitoring measures taken (exogenous risks) and the consideration given to these endogenous risk factors, the incidence of nosocomial infections remains stable or is only slightly on the decrease.

Determining a patient's susceptibility to nosocomial infections is therefore essential in order to be able to offer personalized management and to endeavour to minimise additional risks of a fatal outcome.

To the knowledge of the inventors, the only immunological marker currently known to be associated with increased susceptibility to nosocomial infections is the HLA-DR marker (Human Leukocyte Antigen-DR) whose expression in the monocytes (mHLA-DR) is reduced in patients who develop nosocomial infections. However the expression of this marker, developed by flow cytometry, requires special equipment (flow cytometry) which is not available on biology platforms (use reserved for laboratories specialised in haematology or immunology) and for which there is no standardisation of use. Measurement of mHLA-DR cannot therefore be carried out on a routine basis.

There is therefore a true need for other immunological markers with which it is possible to obtain easy, fast prediction of a patient's susceptibility to nosocomial infections. The ability to identify persons the most at risk of contracting a nosocomial infection would allow the setting up of better adapted and better targeted preventive therapy.

It is within this context that the present invention sets out to provide a novel biomarker to predict the increased risk of a patient developing a nosocomial infection, in particular a patient in hospital intensive care and/or having sustained an insult (surgery, burns, trauma, . . . ) generating a systemic inflammatory response (SIRS), in particular a patient suffering from sepsis, severe sepsis in particular, and preferably a patient with septic shock. Determining the level of expression of this biomarker would therefore allow the easy, rapid determination of a patient's susceptibility to nosocomial infections and the necessary preventive measures to be taken accordingly.

According to a first aspect, the subject of the present invention is therefore a process for determining a patient's susceptibility to nosocomial infections, comprising the following steps:

measuring the expression of sCD127 in a biological sample taken from the patient, or a sample to be tested;

reaching a conclusion on increased susceptibility to nosocomial infections after comparing the expression of sCD127 with a reference value.

The process of the invention for determining susceptibility to nosocomial infections is therefore a process implemented in vitro or ex vivo.

sCD127 is the soluble or plasma form of CD127, an IL-7 receptor. CD127 or alpha chain of the IL-7 receptor is a glycoprotein of 75 kDa and a member of the superfamily of haematopoietic growth factor receptors. It is expressed at the membranes in association with CD132 (common $\gamma_c$ chain) to form the IL-7 receptor. This receptor plays an important role in lymphocyte differentiation, survival and proliferation. CD127 is formed of an extracellular part with 219 amino acids (aa), a transmembrane part with 25 aa and an intracytoplasmic part with 195 aa. The existence of a soluble/plasma form, called sCD127, generated by alternate splicing of the mRNA coding for CD127 was described in 1990 by Goodwin R G et al., *Cell*, 1990, 23, 941-951, but its biological function remains ill-known up until now.

By "nosocomial infection" is meant any infection, chiefly bacterial but also viral and fungal, which occurs in a healthcare facility during or after patient management (diagnosis, therapeutic, palliative, preventive or rehabilitation therapy), and which was neither present nor under incubation at the time patient management was initiated. When the infectious state is not specifically known at the start of patient management, a time of at least 48 hours or a time longer than the incubation period is generally accepted to define a nosocomial infection.

In the meaning of the invention by "systemic inflammatory response" or "SIRS" is meant response associating at least two of the following criteria: Temperature>38° C. or <36° C., Heart rate>90/minute; Respiratory rate>20/minute or paCO2<32 mmHg; White cell count>12.000/mm$^3$ or <4.000/mm$^3$ (Bone et al., *Chest*, 1992, 1644-1655).

In the meaning of the invention by "sCD127" is meant the soluble form or circulating form (also called plasma or serum form) of the IL-7 receptor, also known as the alpha chain of the IL-7 receptor or IL7R or IL7R-ALPHA or IL7RA or CDW127, and in particular such as described by Goodwin et al, Cell, 1990, 23, 941-951 and assayed by Crawley et al, Journal of Immunology, 2010, 184, 4679-4687.

In particular, the reference nucleic sequences for sCD127 according to the invention are preferably the following: Ensembl: ENSG00000168685, HPRD-ID: 00893 Nucleotide sequence: NM 002185.2, Vega genes: OTTHUMG00000090791.

Also the reference protein sequences for sCD127 according to the invention are preferably the following: NP_002176 XP_942460; version: NP_002176.2 GI:28610151.

The sample to be tested using the process of the invention is a biological sample taken from a patient in whom it is desired to determine the susceptibility to nosocomial infections. In particular said biological sample is selected from those likely to contain the sCD127 marker.

The present invention provides a particularly preferred application to patients hospitalised in intensive care and/or having sustained an insult such as surgery, burns, trauma . . . , generating a systemic inflammatory response or SIRS. Therefore the biological sample used in the process of the invention is preferably taken from a patient hospitalized in intensive care and/or having sustained an insult (surgery, burns, trauma . . . ) generating a systemic inflammatory response (SIRS), in particular from a patient suffering from sepsis, particularly severe sepsis, and in particular from a patient in septic shock. In particularly preferred manner the biological sample used in the process of the invention is taken from a patient in septic shock.

According to a first preferred embodiment, the process of the invention allows the determining of a patient's susceptibility to nosocomial infections i.e. reaching the conclusion of an increased risk to nosocomial infections when overexpression of sCD127 is evidenced in the sample to be tested compared with a first reference value.

By "overexpression" is meant a statistically significant increase in the level of expression.

In this embodiment, the first reference value may correspond to the level of sCD127 expression measured in a biological sample taken from a patent hospitalized in intensive care and/or having sustained an insult such as surgery, burns, trauma . . . , generating a systemic inflammatory response or SIRS, who is known not to have developed a nosocomial infection, in particular from a patient with sepsis who is known not to have developed a nosocomial infection, and preferably from a patient with septic shock who is known not to have developed a nosocomial infection. In this case, this measurement of sCD127 expression which forms the first reference value is preferably performed in parallel i.e. performed at the same time as the measurement of sCD127 expression on a sample from a patient for whom it is sought to determine the susceptibility to nosocomial infections, although the taking of the reference sample is prior to the taking of the sample to be tested.

This first reference sample may also correspond to a mean value of the sCD127 expression level which is measured in a pool of samples taken from patients hospitalized in intensive care and/or having sustained an insult such as surgery, burns, trauma . . . , generating a systemic inflammatory response (SIRS) who are known not to have developed a nosocomial infection, in particular from patients with sepsis who are known not to have developed a nosocomial infection, and preferably from patients in septic shock who are known not to have developed a nosocomial infection. In this case, this measurement of sCD127 expression which forms the first reference value is preferably performed prior to the measurement of sCD127 expression in a sample taken from a patient for whom it is sought to determine the susceptibility to nosocomial infections, although the reference samples intended to be "pooled" were taken before the sample to be tested is taken.

In this first preferred embodiment, and in particular to determine the susceptibility to nosocomial infections in a patient with septic shock, the measurement of sCD127 expression in the sample to be tested and optionally in the biological sample used to obtain the first reference value—i.e. when the first reference value is obtained from a biological sample—is performed within 10 days or at day 10 (D10) after septic shock, preferably within 7 days or at day 7 (D7) after septic shock, more preferably within 4 days or at day 4 (D4) after septic shock, and in particular within 3 days or at day 3 (D3) after septic shock.

According to a second preferred embodiment, the process of the invention allows the determining of a patient's susceptibility to nosocomial infections i.e. reaching the conclusion of an increased risk of developing a nosocomial infection or increased susceptibility to nosocomial infections, when the expression of sCD127 measured in the sample to be tested is not significantly decreased compared with a second reference value. In particularly preferred manner the conclusion is reached of an increased risk of developing a nosocomial infection if the expression of sCD127 measured in the sample to be tested is not reduced by more than 25% and in particular not reduced by more than 20% compared with this second reference value.

This second reference value may correspond to the level of sCD127 expression measured in a biological sample taken from the same said patient taken previously i.e. a biological sample taken prior to the biological sample that is to be tested. By "previously" or "prior" is meant at an earlier time or before the taking of the sample to be tested.

In this second preferred embodiment, and in particular to determine the susceptibility to nosocomial infections of a patient with septic shock, the measurement of sCD127 expression in the sample to be tested is performed at or at about day 10 (D10) after septic shock, preferably at or at about day 7 (D7) after septic shock, more preferably at or at about day 4 (D4) after septic shock.

The prior sampling can be performed for example within or at 48 h after septic shock and at least 24 h before taking the sample to be tested, and preferably the prior sampling is performed within or at 48 h after septic shock and the sample to be tested is taken within 48 h after the prior sampling or at 48 h after the prior sampling.

Therefore in all cases, before actual measuring of sCD127 expression in the sample to be tested, the process of the invention may comprise the prior obtaining of the reference value, whether this is the first reference value or the second reference value, against which the expression level detected in the tested sample will be compared so that a conclusion can be reached on whether or not there is an increased risk that the patient, from whom the sample to be tested was taken, will develop a nosocomial infection.

It is therefore against these reference values, whether the first reference value or the second reference value obtained previously or at the same time that the value of sCD127 expression measured in the sample to be tested will be compared.

The sample in which the process of the invention is implemented, also called herein the sample to be tested, may be of human or animal origin and preferably human.

Therefore the sample to be tested may be of different types. In particular this sample is a biological fluid selected for example from among blood, whole blood (such as collected via venous route i.e. containing white and red cells, platelets and plasma), serum, plasma and bronchoalveolar lavage fluid.

Preferably the sample to be tested taken from said patient is a plasma or serum sample.

The samples from which the reference values can be determined, whether the first reference value or the second reference value, also called "reference samples" may be of different types and in particular of biological type as aforementioned for the sample to be tested (biological fluids). Advantageously these biological samples are of the same type as the biological sample to be tested or at least of compatible type to form a reference for the detection and/or quantification of sCD127 expression.

To obtain the first reference value in particular, these samples are preferably taken from persons having the same characteristics or a majority of common characteristics, notably of same gender and/or of similar or same age and/or of same ethnic origin as the subject or patient in whom it is desired to determine the susceptibility to nosocomial infections. The reference sample in this case may also be formed by any sample, whether biological or not, previously calibrated to contain a mean sCD127 value which corresponds to the level measured in a pool of biological samples taken from patients hospitalized in intensive care and/or having sustained an insult such as surgery, burns, trauma . . . , generating a systemic inflammatory response (SIRS) who are known not to have developed a nosocomial infection, in particular from patients with sepsis who are known not to have developed a nosocomial infection, and preferably from patients with septic shock who are known not to have developed a nosocomial infection. In this case and according to one particularly preferred variant, the reference sample is taken from one or more patients with septic shock who are known not to have developed a nosocomial infection.

To obtain the second reference value in particular, the reference sample is a biological sample taken from the same said patient, i.e. from the patient for whom it is desired to determine the susceptibility to nosocomial infections and from whom the sample to be tested is taken, this reference sample being a prior sample i.e. a biological sample taken at an earlier time before the sample to be tested.

In the meaning of the present invention, by the term "measuring the expression" is meant in vitro or ex vivo measurement. Also this term is intended to designate the detection and quantification of sCD127 at protein level. For this purpose any detection and/or quantification method well known to the person skilled in the art can be used to implement the invention, whether to determine the presence of and/or to measure the expression of the sCD127 protein. As an example of method to measure the expression of the sCD127 protein, particular mention can be made of the method described by Crawley et al, *Journal of Immunology*, 2010, 184, 4679-4687.

In particular, measurement of the level of sCD127 expression is performed using sCD127-specific tools or reagents allowing the direct or indirect determination of its presence and/or quantification of the level of expression thereof.

Amongst these tools or reagents capable of detecting and/or quantifying sCD127, particular mention can be made of specific polyclonal or monoclonal antibodies, preferably monoclonal, or fragments or derivatives thereof, e.g. "single chain" antibodies Sv.

Amongst these tools or reagents preference is particularly given to those which are specific to the soluble form of the IL-7 receptor, i.e. which do not recognize CD127 which is the non-soluble cellular/membrane form of this receptor. It is nevertheless possible to use tools or reagents which recognize both the soluble form sCD127 and the cellular form CD127 of the IL-7 receptor, provided it is possible to distinguish between these two forms by other means such as the type of analyzed sample (e.g. plasma or serum versus biological sample containing cells or whole blood).

When the detection and/or quantification of sCD127 is performed at protein level, the standard techniques such as Western-Blot, ELISA, RIA, IRMA, FIA, CLIA, ECL, flow cytometry or immunocytology can be used.

In particularly advantageous manner, the expression of sCD127 is measured at protein level and preferably using an ELISA technique.

According to the invention and in particular in this particular embodiment, the level of sCD127 expression is preferably measured using monoclonal or polyclonal anti-sCD127 antibodies, and in particular monoclonal anti-sCD127 antibodies. For example particular mention can be made of the human R34.34 monoclonal anti-CD127 antibodies marketed by Beckman Coulter® or the polyclonal anti-CD127 antibodies marketed by R&D Systems®.

All the aforementioned indications and preferences concerning the measurement of sCD127 expression apply indifferently, whether for measurement of said expression in the sample to be tested or in the reference sample.

According to a second aspect, a further subject of the invention is the use of in vitro or ex vivo measurement of sCD127 expression to determine a patient's susceptibility to nosocomial infections.

Preferably, this use is particularly advantageous to determine the susceptibility to nosocomial infections of a patient hospitalized in intensive care and/or having sustained an insult such as surgery, burns, trauma . . . , generating a systemic inflammatory response or SIRS, in particular a patient with sepsis, in particular severe sepsis, and preferably a patient in septic shock. Preferably the use of the invention allows determining of the susceptibility to nosocomial infections of a patient in septic shock.

Additionally, for the use according to the invention the expression of sCD127 is preferably measured at protein level and in particular using an ELISA technique.

In particular, sCD127 expression can be measured using monoclonal or polyclonal anti-sCD127 antibodies, and preferably monoclonal anti-sCD127 antibodies. The aforementioned antibodies can also be used for this second aspect of the invention.

More broadly all the preferred embodiments mentioned above, concerning the process and the combinations thereof, also form preferred embodiments of the use of the invention.

According to a third aspect, a further subject of the present invention is a kit for in vitro or ex vivo measurement of sCD127 expression in a biological sample, comprising:
  specific tools or reagents allowing measurement of sCD127 expression in said biological sample; and
  a positive standard sample which is a sample calibrated to contain the amount of sCD127 which corresponds to the mean amount measured in a pool of samples from patients who are known to have developed a nosocomial infection, and/or a negative standard sample which is a sample calibrated to contain the amount of sCD127 which corresponds to the mean amount measured in a pool of samples from patients who are known not to have developed a nosocomial infection.

The kit of the invention therefore comprises specific tools or reagents allowing the measurement of sCD127 expression in said biological sample, and at least one standard sample.

The kit of the invention particularly allows determination of a patient's susceptibility to nosocomial infections and in particular a patient in septic shock.

Preferably the specific tool or reagents allowing measurement of sCD127 expression in a biological sample and contained in the kit of the invention allow the detection and/or quantification of sCD127 expression, whether at protein level or at sCD127 activity level, and preferably at protein level.

According to one particularly preferred embodiment, the kit of the invention contains monoclonal or polyclonal anti-sCD127 antibodies, and in particular monoclonal antibodies.

Another positive standard sample may also be a sample taken from a patient who is known to have developed a nosocomial infection. Similarly, another negative standard sample may also be a sample taken from a patient known not to have developed a nosocomial infection. Whether for a positive or negative standard, this type of standard sample is preferably taken from one or more patients hospitalized in intensive care and/or having sustained an insult such as surgery, burns, trauma . . . , generating a systemic inflammatory response (SIRS), in particular from one or more patients with sepsis and preferably from one of patients in septic shock. For example, the kit may contain a negative standard sample taken from one or more patients hospitalized in intensive care and/or having sustained an insult such as surgery, burns, trauma . . . , generating a systemic inflammatory response (SIRS), who are known not to have developed a nosocomial infection, in particular taken from one or more patients in septic shock known not to have developed a nosocomial infection.

Preferably the kit comprises both a positive standard sample and a negative standard sample and in particular each chosen from among the calibrated samples such as defined above.

The invention also covers the use of a kit of the invention to implement the process of the invention, and in particular to determine a patient's susceptibility to nosocomial infections, preferably a patient hospitalized in intensive care and/or having sustained an insult such as surgery, burns, trauma . . . , generating a systemic inflammatory response syndrome (SIRS), in particular a patient with sepsis, particularly severe sepsis, and preferably a patient in septic shock. Preferably the use of the kit of the invention allows the determination of susceptibility to nosocomial infections of a patient in septic shock.

All the preferred embodiments mentioned above concerning the process and the combinations thereof also form preferred embodiments of the kit of the invention and of the use thereof.

Figure 1B:
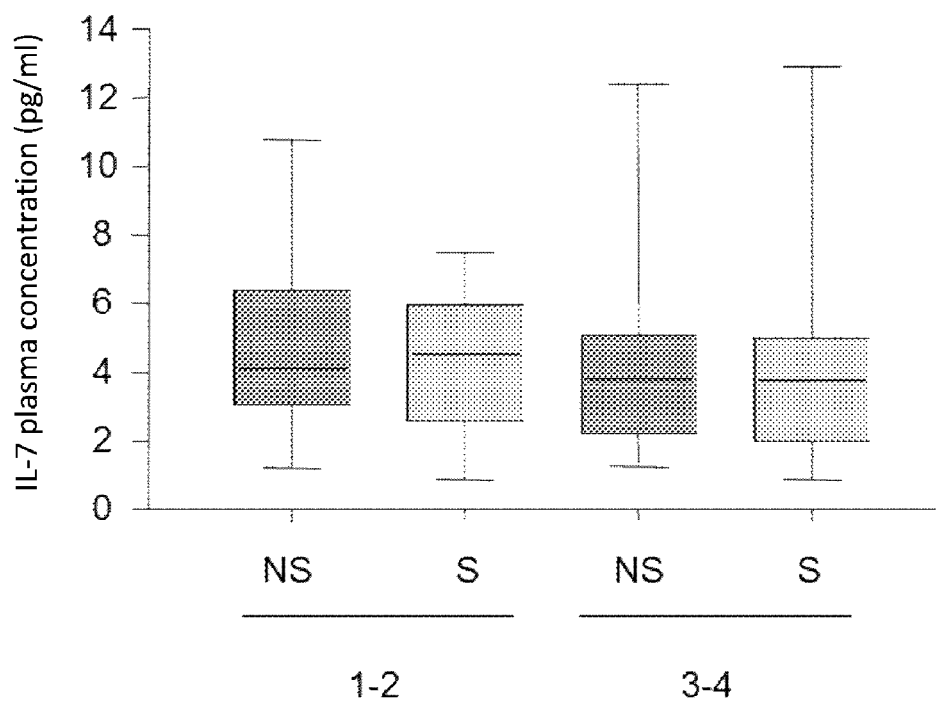
Figure 1C:
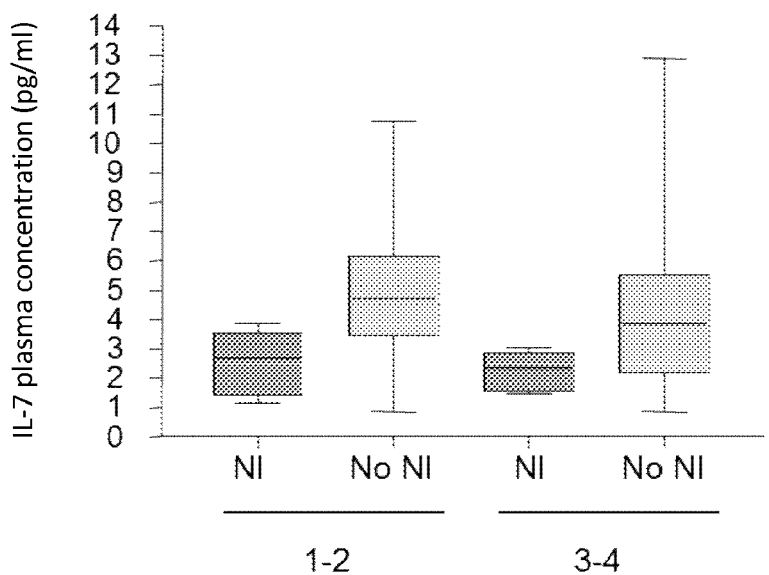

Various other characteristics will become apparent from the description given below with reference to the appended Figures which, as non-limiting examples, illustrate embodiments of the subject of the invention and in which:

FIG. 1 shows the IL-7 plasma concentration in 35 patients in septic shock at days 1-2 (1-2) and 3-4 (3-4) and in 30 healthy volunteers "HV" (A), and the comparison of these results between "NS" and "S" patient groups (FIG. 1B) and "NI" and "No NI" patient groups (FIG. 1C).

Figure 2A:
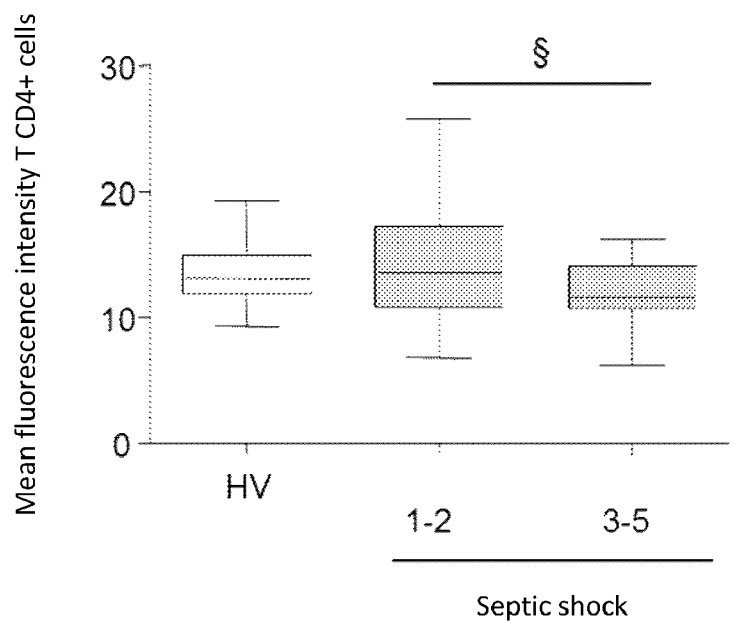
Figure 2B:
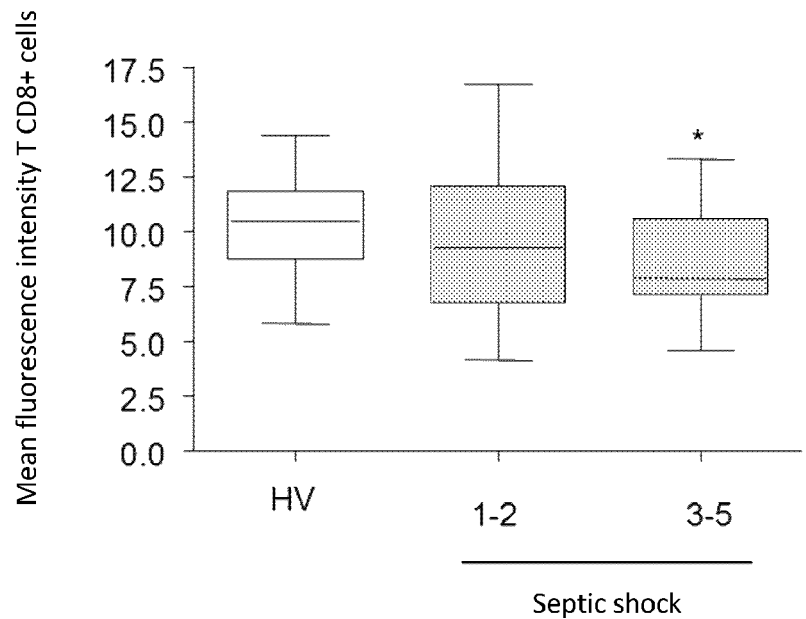

** $p<0.005$ vs. "HV"—Mann Whitney U-test;

FIG. 2 gives the expression of CD127 in T CD4$^+$ cells (FIG. 2A) and T CD8$^+$ cells (FIG. 2B) in 35 patients with septic shock at days 1-2 and 3-5 and in 30 healthy volunteers "HV".

* $p<0.05$ vs. "HV"—Mann Whitney U-test; §$p<0.05$—trend in time within one same group of patients—Wilcoxon paired t-test.

Figure 3A:
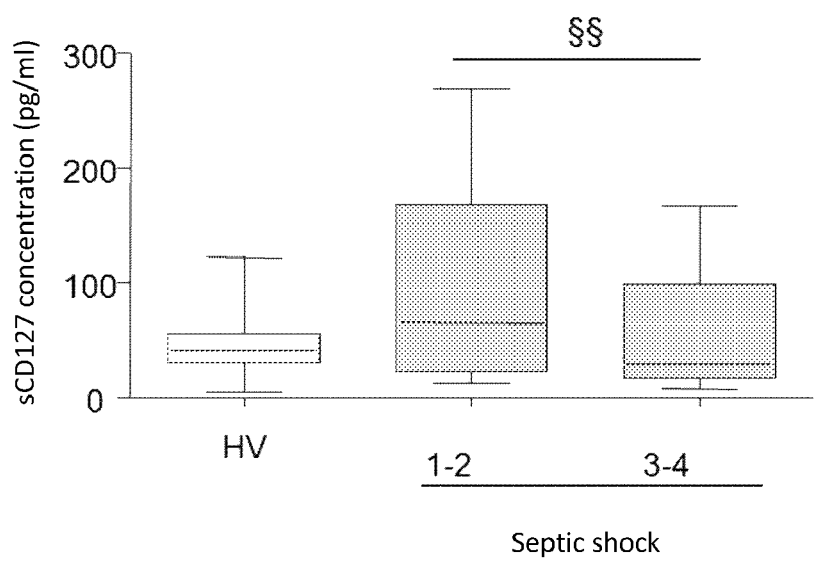
Figure 3B:
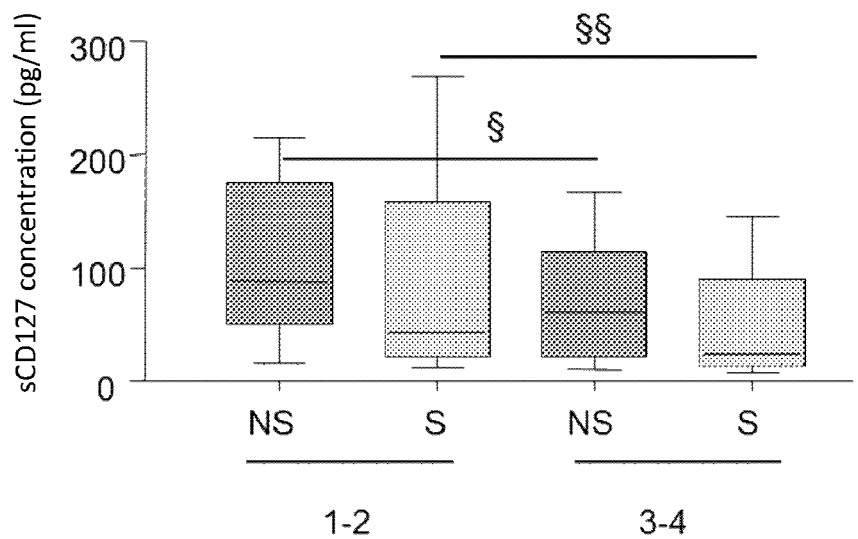
Figure 3C:
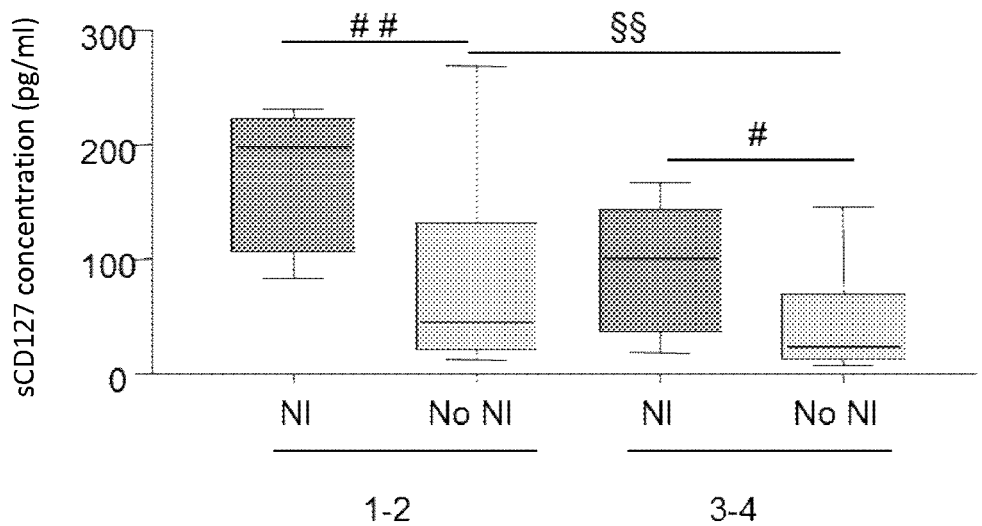

FIG. 3 gives the sCD127 plasma concentration in 35 patients with septic shock at days 1-2 and 3-4, and in 30 healthy volunteers (FIG. 3A) and the comparison of these results between the "NS" or "S" patient groups (FIG. 3B) and "NI" or "No NI" patient groups (FIG. 3C).

$p<0.05$ ## $p<0.005$ vs. "No NI"—Mann Whitney U-test; §$p<0.05$ §§$p<0.005$—trend in time within one same group of patients—Wilcoxon paired t-test.

Figure 4:
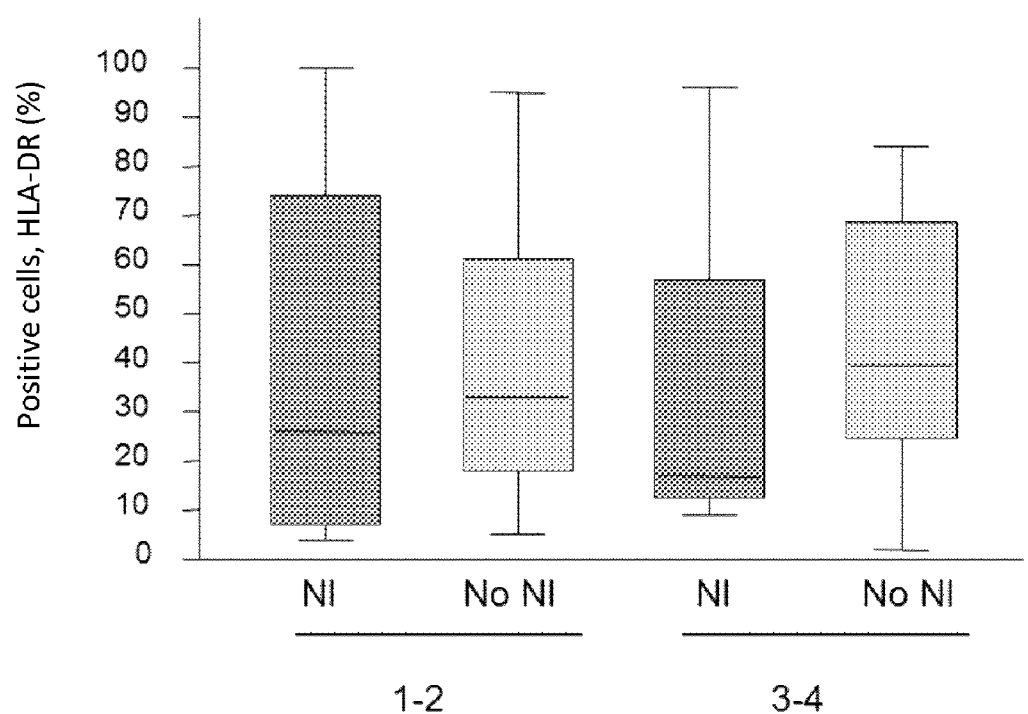

FIG. 4 shows the expression of the HLA-DR marker in 35 patients with septic shock at days 1-2 and 3-4, and in 30 healthy volunteers as per patient groups "NI" or "No NI".

METHODS

Measurement of IL-7 Plasma Concentration

The IL-7 plasma concentration was measured with a kit using the LUMINEX™ technique marketed by Bio-Rad (Bio-Plex Pro Cytokine, Chemokine and Growth Factor Assays: BioPlex Pro Reagent kit, Bio-Rad #171-304070 and SinglePlex IL-7) following the supplier's directions.

Measurement of Cell Expression of the IL-7 Receptor (CD127)

In brief, 50 µl of whole blood were incubated in the presence of 5 µl of anti-CD4 antibody conjugated with Phycoerythin-TexasRed (ECD) (Beckman Coulter #6604727) or 5 µl of ECD-conjugated anti-CD8 antibody (Beckman Coulter #737659) and 10 µl of anti-CD127 antibody conjugated with phycoerythrin (PE) (Beckman Coulter #IM1980U) for 15 minutes at ambient temperature and in the dark. The red blood cells were then lysed by hypotonic lysis and the cells fixed by automatic lysis on TQ-Prep automated system (Beckman Coulter). The membrane expression of CD127 on the surface of the T CD4+ or CD8+ lymphocytes was measured by flow cytometry.

Assay of the Soluble Form of the IL-7 Receptor (sCD127) by ELISA

Coating

A coating buffer was prepared to contain 0.8 g of $Na_2CO_3$, 1.4 g $NaHCO_3$, 0.1 g $NaN_3$ in 500 ml of water (pH 9.6).

100 µL of capture antibody (Ab) (Mouse Monoclonal Antibody Anti-CD127, human, R34.34, Beckman Coulter®) diluted in coating buffer were deposited per well of an assay plate ([Ab]=8 µg/mL). The plate was then covered for incubation at 4° C. overnight.

The content of the wells was then aspirated and the wells washed 3 times with at least 300 µL of 0.05% PBS-TWEEN20® non-ionic detergent wash buffer. All the liquid was carefully removed at each wash. After the last wash the plate was turned over onto absorbent paper to remove all traces of buffer.

Blocking

Non-specific fixing was blocked using 150 µL of blocking buffer per well (10% foetal bovine serum (FBS)/0.05% PBS-TWEEN20® non-ionic detergent), and the plate incubated for 1 h at 37° C.

The content of the wells was again aspirated and the wells washed 3 times with at least 300 µL of 0.05% PBS-TWEEN20® non-ionic detergent wash buffer. All the liquid was carefully removed at each wash. After the last wash, the plate was turned over onto absorbent paper to remove all traces of buffer.

Samples and Standards

A standard range was obtained with recombinant human IL-7Rα/CD127 Fc chimera (R&D Systems—Catalog Number: 306-IR) diluted in PBS containing 5% FCS diluting buffer, as described in Table 1 below and in accordance with C. Janot-Sardet et al. *Journal of Immunological Methods*, 2010, 28, 115-123.

TABLE 1

| | rh IL-7Rα/CD127 Fc chimera | | | | | | | |
|---|---|---|---|---|---|---|---|---|
| [c] (ng/mL) | 500 | 250 | 125 | 62.5 | 31.25 | 15.7 | 7.85 | 0 |
| Diluent (µL) | 0 | 100 | 100 | 100 | 100 | 100 | 100 | 100 |

TABLE 1-continued

| | rh IL-7Rα/CD127 Fc chimera | | | |
|---|---|---|---|---|
| 500 ng/mL solution (μL) | 100 | 100 | Successive dilutions | 0 |

100 μL of sample or standard (extemporaneously-reconstituted solution of CD127 Fc chimera aliquoted at concentrations of 60 ng/ml and 10 ng/ml) were added to each well and the plate incubated for 1 h at 37° C.

The content of the wells was again aspirated and the wells washed 3 times with at least 300 μL of 0.05% PBS-TWEEN20® non-ionic detergent wash buffer. All the liquid was carefully removed at each wash. After the last wash the plate was turned over onto absorbent paper to remove all traces of buffer.

Detection Antibody

100 μL of detection antibody (biotinylated polyclonal anti-CD127 goat antibody reconstituted with 1 mL of 1% TBS-BSA, R&D Systems®) diluted in PBS/5% FBS, were added to each well ([Ab]=200 ng/mL), and the plate then incubated for 1 h at 37° C.

The content of the wells was again aspirated and the wells washed 3 times with at least 300 μL of 0.05% de PBS-TWEEN20® non-ionic detergent wash buffer. All the liquid was carefully removed at each wash. After the last wash the plate was turned over onto absorbent paper to remove all traces of buffer.

Detection

100 μL of Streptavidin-HRP were added to each well ([Streptavidin-HRP]=8 μL/mL). The plate was covered to be incubated for 30 min at ambient temperature.

The content of the wells was again aspirated and the wells washed 3 times with at least 300 μL of 0.05% PBS-TWEEN20® non-ionic detergent wash buffer. All the liquid was carefully removed at each wash. After the last wash the plate was turned over onto absorbent paper to remove all traces of buffer. At this washing step the wells were impregnated with the wash buffer 1 to 2 min before aspiration.

The two bottles of TMB colorimetric substrate solution (3,3',5,5'-tetramethylbenzidine, bioMérieux #XX7LF1UC) were volume/volume mixed. 100 μL of this substrate solution were deposited in each well. The plate was covered to be incubated 30 min at ambient temperature.

Finally, plate read-off was performed by absorbance measurement at 450 nm.

Measurement of the Monocyte Expression of HLA-DR

Measurement was performed by the flow cytometry technique, using direct staining with EDTA whole blood.

The two following antibodies were incubated with 50 μL of whole blood (30 minutes at ambient temperature and in the dark):
- 5 μL of fluorescein-conjugated anti-CD14 antibody (Beckman Coulter Immunotech—Ref.: IM0645), allowing identification of the monocytes among the white blood cells);
- 10 μL of phycoerythrin-conjugated anti-HLA-DR antibody (Becton Dickinson—Ref.: 347401), allowing quantification of HLA-DR expression on the surface of the cells.

The red blood cells were then removed: lysis by adding 1 ml of lysis solution (marketed by Becton Dickinson under reference 349202), 1:10 dilution, 15 minutes at ambient temperature and in the dark.

The cells were then analysed on a flow cytometer (FC500—Beckman Coulter).

Results are expressed as a % of positive cells, the positivity threshold being defined by isotype control (Mouse IgG2a PE Becton Dickinson—Ref.: 349053).

Results

Plasma samples were taken from 35 patients in septic shock at days 1-2 (D1-2) and 3-4 (D3-4) after septic shock and then stored (retrospective cohort). Different parameters or markers were measured such as IL-7 and sCD127 plasma concentrations, and CD127 expression on T CD4$^+$ cells, and HLA-DR expression on the monocytes. At 28 days after admission into intensive care for septic shock, 13 patients did not survive ("NS") i.e. 37% whereas 22 patients did survive ("S") out of 35 patients. 6 patients contracted a nosocomial infection ("NI") i.e. 17%, whereas 29 patients remained free of any nosocomial occurrence ("No NI").

The same measurements were performed in 30 healthy volunteers (HV).

The results obtained were compared using a Mann Whitney U-test in these different populations of volunteers or patients, and are grouped together in appended FIGS. 1 to 4.

These results show that the IL-7 plasma concentration is significantly reduced (at D1-2), but not significantly at D3-4 in patients who develop secondary nosocomial infection compared with patients who did not suffer any nosocomial infection occurrence (FIG. 1C), whereas it remained unchanged between the surviving patients "S" and non-surviving patients "NS".

In addition, the cell expression of the IL-7 receptor (CD127) was maintained after septic shock (FIGS. 2A and 2B), and without any difference between the surviving patients "S" and non-surviving patients "NS" or the patients who did "NI" or did not "No NI" develop nosocomial infections (results not shown).

The slight increase in the plasma concentration of the soluble form of the I-7 receptor, or sCD127, observed at the onset of septic shock is not statistically significant and returns to "normal" values over time (FIG. 3A).

On the other hand, whereas the plasma concentration of sCD127 remained unchanged between the surviving patients "S" and non-surviving patients "NS" (FIG. 3B), a marked increase in the plasma concentration of sCD127 was observed in "NI" patients who developed a nosocomial infection compared with the "No NI" patients who did not contact a nosocomial infection (FIG. 3C).

Also it was observed that the plasma concentration of sCD127 does not change over time (between D1-2 and D3-4) in "NI" patients who developed a nosocomial infection, contrary to the "No NI" patients who did not contract a nosocomial infection (FIG. 3C).

By way of comparison, study of the expression of the prior art marker HLA-DR on the same cohort of patients did not allow evidencing of the reduction in expression of this marker between the "NI" patients who suffered a nosocomial infection and the "No NI" who did not contract a nosocomial infection (FIG. 4), contrary to what is clearly established in the prior art.

This difference, probably related to the size of the cohort studied herein which is smaller compared with the cohorts analysed in prior art studies, allows evidencing of the pertinence of the sCD127 marker compared with HLA-DR. Despite the size of the cohort studied herein the results show that the study of the expression of sCD127 according to the invention is informative with regard to the susceptibility of patients to nosocomial infections.

It follows that all these results show that measurement of sCD127 expression is a useful immunological marker to determine the susceptibility of a patient to nosocomial infections, and in particular patients hospitalized in intensive care and/or having sustained an insult (surgery, burns, trauma, . . . ) generating a systemic inflammatory response (SIRS), and in particular patients with sepsis, particularly severe sepsis, and preferably patients in septic shock.

The invention is not limited to the examples described and illustrated since various modifications can be made thereto without departing from the scope of the invention.

The invention claimed is:

1. A process for determining the susceptibility of a patient with septic shock to nosocomial infections, comprising the following steps:
    taking a first biological sample from said patient up to 48h after an onset of septic shock;
    taking a second biological sample from said patient at least 24h after the first biological sample is taken, and up to 10 days after the onset of septic shock; and
    measuring the expression of soluble CD127 in the first biological sample and in the second biological sample using anti-soluble CD127 antibodies, whereby a concentration of soluble CD127 in the first biological sample and a concentration of soluble CD127 in the second biological sample is obtained;
    wherein an increased susceptibility to nosocomial infections in the patient is indicated when the concentration of soluble CD127 in the second biological sample is not significantly reduced compared to the concentration of soluble CD127 in the first biological sample.

2. The process according to claim 1, wherein the expression of soluble CD127 in the second biological sample is measured within 10 days after septic shock, or at day 10 after septic shock.

3. The process according to claim 1, wherein the expression of soluble CD127 in the second biological sample is measured within or at about 7 days after septic shock.

4. The process according to claim 1, wherein the second biological sample is taken from said patient within 48h of taking the first biological sample, or at 48h after the first biological sample is taken.

5. The process according to claim 1, wherein the second biological sample is a plasma sample or a serum sample.

6. The process according to claim 1, comprising measuring the expression of soluble CD127 using an ELISA technique.

7. The process according to claim 1, comprising measuring the expression of soluble CD127 using monoclonal antibodies.

8. The process according to claim 1, wherein the increased susceptibility to nosocomial infections in the patient is indicated when the expression of soluble CD127 measured in the second biological sample is not reduced by more than 25%, compared with the expression of soluble CD127 measured in the first biological sample.

9. The process according to claim 1, wherein the increased susceptibility to nosocomial infections in the patient is indicated when the expression of soluble CD127 measured in the second biological sample is not reduced by more than 20%, compared with the expression of soluble CD127 measured in the first biological sample.

10. The process according to claim 1, wherein the expression of soluble CD127 in the second biological sample is measured within 4 days, or at day 4 after septic shock.

11. The process according to claim 1, wherein the expression of soluble CD127 in the second biological sample is measured within 3 days, or at day 3, after septic shock.

* * * * *